United States Patent
Hong et al.

(10) Patent No.: US 11,104,846 B2
(45) Date of Patent: Aug. 31, 2021

(54) QUANTUM DOTS IN WHICH IONIC LIQUIDS ARE ION-BONDED AND THEIR PREPARATION METHOD

(71) Applicants: SHIN-A T&C, Seoul (KR); UNIAM, Seoul (KR)

(72) Inventors: Seung Mo Hong, Incheon (KR); Jin Han Song, Seoul (KR); Sung Hun Choi, Cheonan-si (KR); Hyeok Jin Hong, Suwon-si (KR)

(73) Assignees: SHIN-A T&C, Seoul (KR); UNIAM, Seoul (KR)

( * ) Notice: Subject to any disclaimer, the term of this patent is extended or adjusted under 35 U.S.C. 154(b) by 0 days.

(21) Appl. No.: 16/741,935

(22) Filed: Jan. 14, 2020

(65) Prior Publication Data

US 2020/0224095 A1    Jul. 16, 2020

(30) Foreign Application Priority Data

Jan. 16, 2019  (KR) .................. 10-2019-0005902

(51) Int. Cl.
  *C09K 11/02*  (2006.01)
  *C09K 11/70*  (2006.01)
  (Continued)

(52) U.S. Cl.
  CPC .............. *C09K 11/02* (2013.01); *B82Y 40/00* (2013.01); *C07D 233/58* (2013.01);
  (Continued)

(58) Field of Classification Search
  None
  See application file for complete search history.

(56) References Cited

U.S. PATENT DOCUMENTS

| 6,251,303 B1 * | 6/2001 | Bawendi ................ | B82Y 15/00 252/301.4 R |
| 6,955,855 B2 * | 10/2005 | Naasani ................. | B82Y 15/00 252/301.4 R |

(Continued)

FOREIGN PATENT DOCUMENTS

| EP | 3221421 B1 | 6/2019 |
| KR | 10-2011-0082452 A | 7/2011 |

(Continued)

OTHER PUBLICATIONS

English machine translation of Suh et al. (KR 20110082452 A) retrieved online from Espacenet; pp. 1-11. (Year: 2011).*

(Continued)

*Primary Examiner* — Katie L. Hammer
(74) *Attorney, Agent, or Firm* — Sughrue Mion, PLLC

(57) ABSTRACT

A quantum dot particle in which an ionic liquid is ion-bonded is disclosed. The quantum dot particle includes a quantum dot having a core/shell nanostructure; and an ionic liquid compound represented by following Chemical Formula 1, bonded to the surface of the quantum dot, wherein the quantum dot and the ionic liquid compound form an ionic bond:

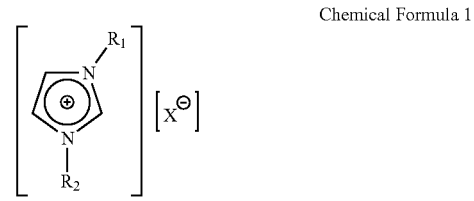

Chemical Formula 1 wherein,
$R^1$ and $R^2$ are each independently a branched or unbranched hydrocarbon group having 1 to 22 carbon atoms, and $X^-$ is a monovalent anion, wherein the hydrocarbon group includes a saturated or unsaturated group and may include one or more hetero atoms.

13 Claims, 5 Drawing Sheets

(51) Int. Cl.
    *C09K 11/88*     (2006.01)
    *H01L 31/0352*     (2006.01)
    *C07D 233/58*     (2006.01)
    *C09K 11/08*     (2006.01)
    *B82Y 40/00*     (2011.01)
    *B82Y 20/00*     (2011.01)
    *B82Y 30/00*     (2011.01)

(52) U.S. Cl.
    CPC ............ *C09K 11/025* (2013.01); *C09K 11/08* (2013.01); *C09K 11/70* (2013.01); *C09K 11/883* (2013.01); *H01L 31/035218* (2013.01); *B82Y 20/00* (2013.01); *B82Y 30/00* (2013.01); *Y10S 438/962* (2013.01)

(56) References Cited

U.S. PATENT DOCUMENTS

| | | |
|---|---|---|
| 7,557,028 B1 | 7/2009 | Scher et al. |
| 7,645,397 B2 | 1/2010 | Parce et al. |
| 8,062,967 B1 | 11/2011 | Scher et al. |
| 2006/0014315 A1* | 1/2006 | Chan ............... B82Y 10/00 438/99 |
| 2006/0216759 A1* | 9/2006 | Naasani ............... C09K 11/883 435/7.5 |
| 2010/0276638 A1 | 11/2010 | Liu et al. |
| 2014/0051883 A1* | 2/2014 | Kim ................ C07C 319/06 562/106 |
| 2015/0298988 A1* | 10/2015 | Helms ............ C01B 19/007 252/519.12 |
| 2018/0033856 A1 | 2/2018 | Kwon et al. |
| 2019/0233613 A1* | 8/2019 | Odent ................ C08K 3/36 |

FOREIGN PATENT DOCUMENTS

| | | |
|---|---|---|
| KR | 10-1627103 B1 | 6/2016 |
| KR | 10-2018-0013801 A | 2/2018 |
| KR | 10-2018-0016196 A | 2/2018 |

OTHER PUBLICATIONS

Baogang Wang, et al., "Tunable Amphiphilicity and Multifunctional Applications of Ionic-Liquid-Modified Carbon Quantum Dots", ACS Applied Materials and Interfaces, 2015, pp. 6919-6925, vol. 7, No. 12.

Zengchun Xie, et al., "Ionic liquid-functionalized carbon quantum dots as fluorescent probes for sensitive and selective detection of iron ion and ascorbic acid", Colloids and Surfaces A: Physicochemical and Engineering Aspects, 2017, pp. 38-44, vol. 529.

* cited by examiner

[Fig. 1]
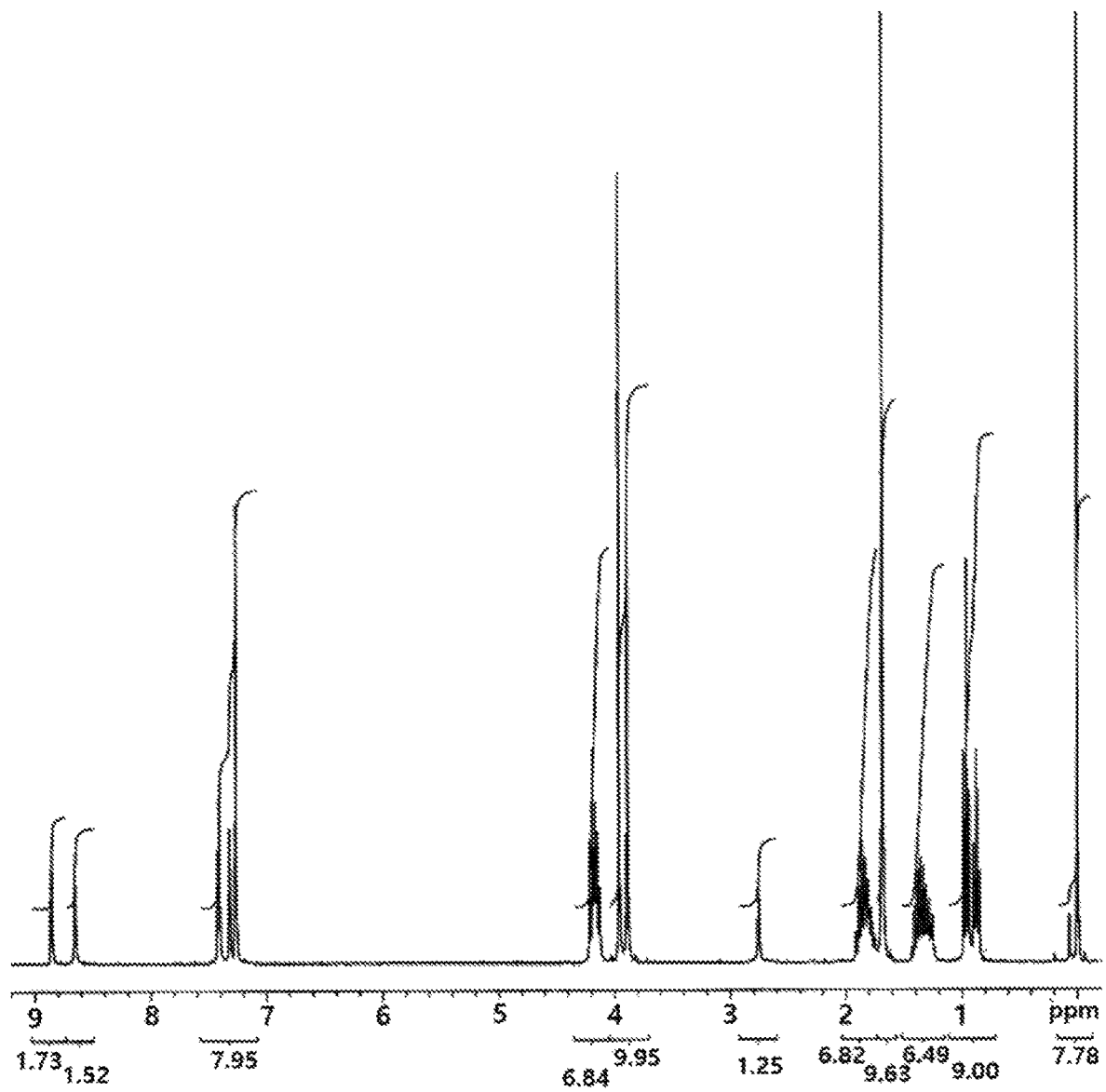

[Fig. 2]
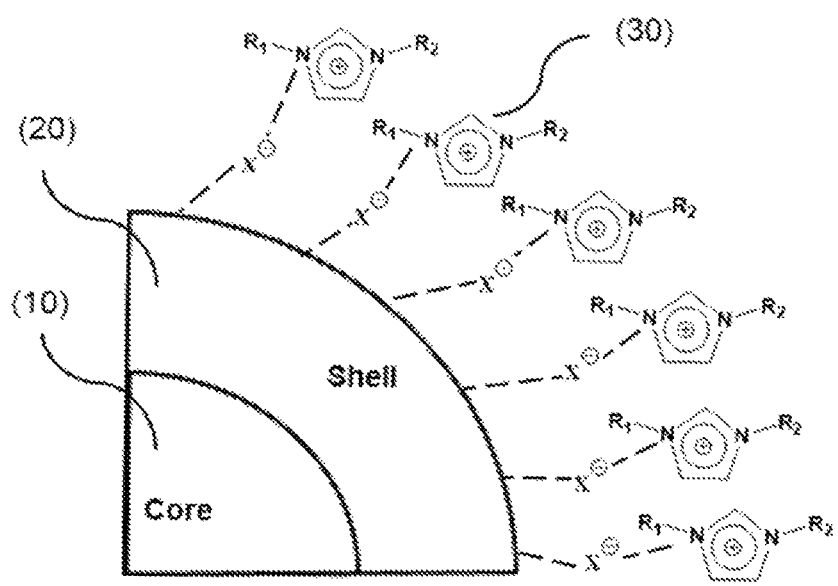

[Fig. 3]
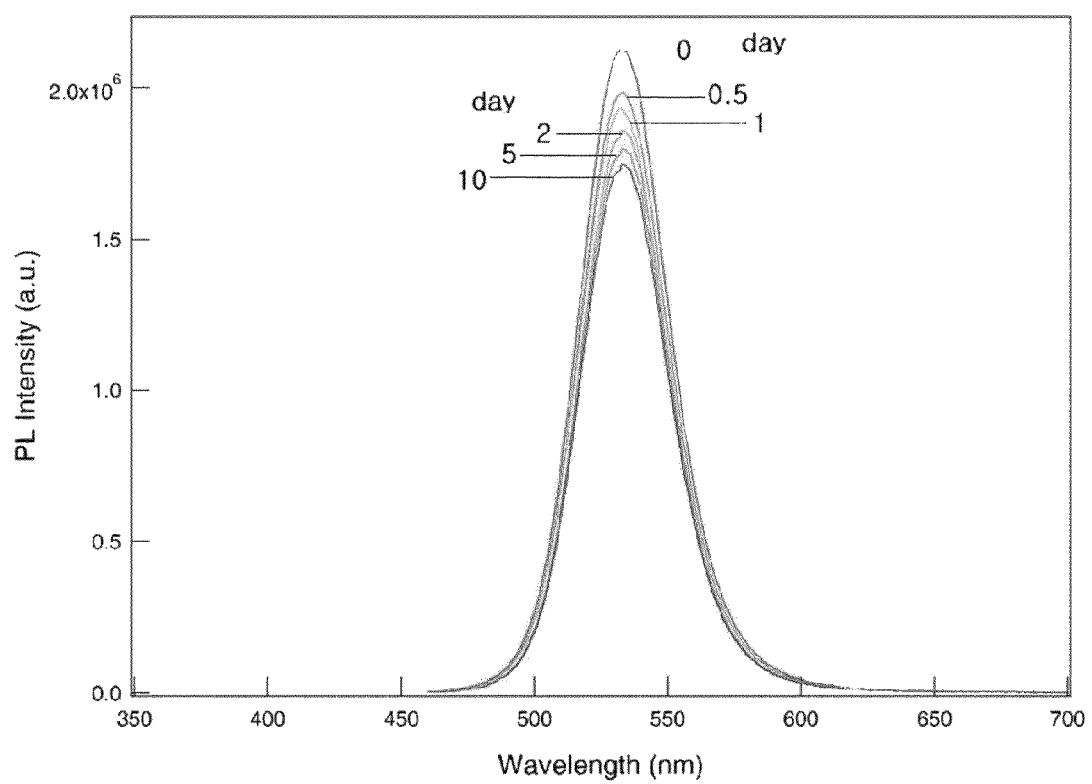

【Fig. 4】
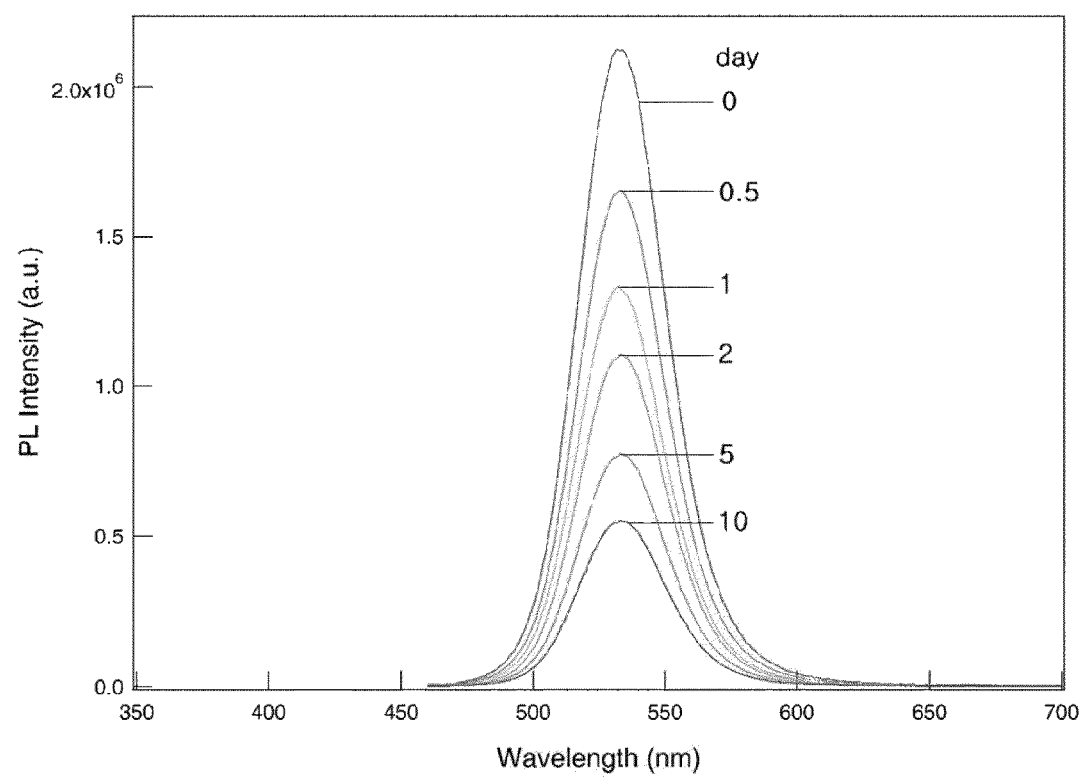

[Fig. 5]
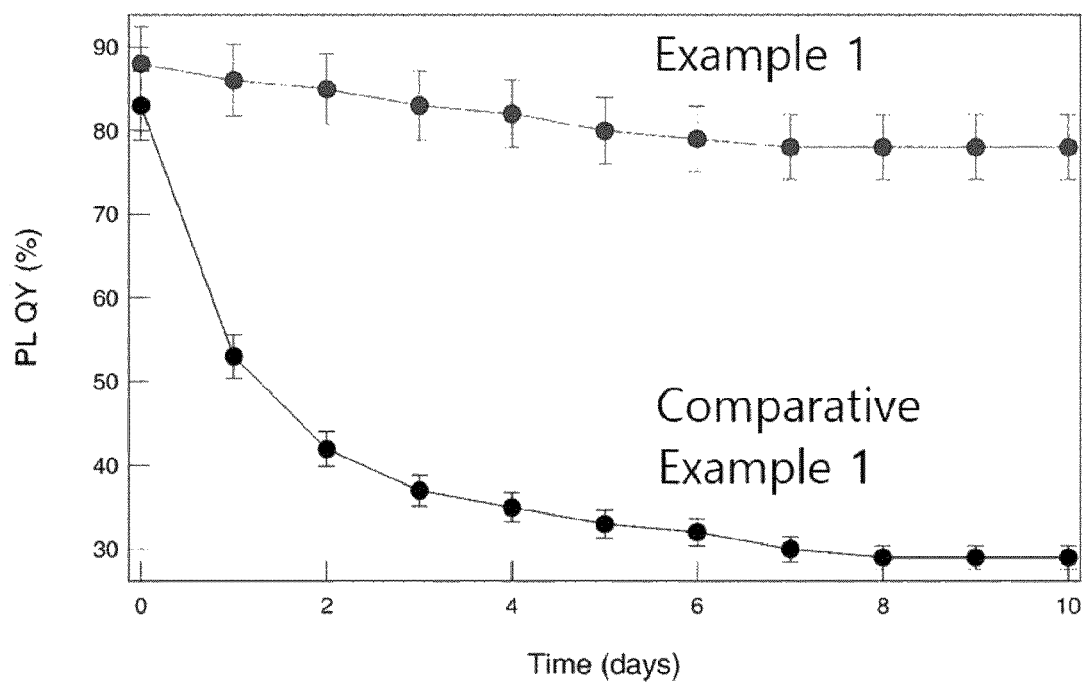

QUANTUM DOTS IN WHICH IONIC LIQUIDS ARE ION-BONDED AND THEIR PREPARATION METHOD

CROSS REFERENCE TO RELATED APPLICATIONS

This application claims priority based on Korean Patent Application No. 10-2019-0005902 filed Jan. 16, 2019, content of which is incorporated herein by reference.

TECHNICAL FIELD

The present invention relates to a quantum dot in which an ionic liquid is ion-bonded, and a method of preparing the same.

BACKGROUND ART

A quantum dot (QD) is a several nanoscale semiconducting nanosized particle having a quantum confinement effect, and exhibits excellent optical and electrical properties that a general semiconducting material does not have in the bulk state. The quantum dot can emit light when stimulated with energy such as light, and the color of light to be emitted varies according to the size of the particle. In the case of utilizing such a quantum dot, since a large area high resolution display having good color purity, excellent color reproducibility, and good video characteristics can be implemented, a lot of researches on the quantum dot have been conducted.

As a quantum dot light-emitting material, Groups II-VI compound semiconductors having high quantum efficiency and excellent stability are mainly used, in particular, a quantum dot material of a core-shell structure using Cd such as CdSe/ZnS and CdZnS/ZnS as a core material has been studied extensively due to its high PL (photoluminance) quantum efficiency. However, since Cd is harmful to the human body, development of a quantum dot material that does not use Cd, and an element and a device using the same is in progress and in mass production.

Meanwhile, in the quantum dot of the core-shell structure, the shell serves to protect an electron and a hole of the core from the outside, but the core and the shell may be oxidized by the external environment to reduce the quantum efficiency. Therefore, a shell process to coat an inorganic shell of ZnS or ZnSSe as an outer layer is added to protect the core (for example, InP), or a method of binding a ligand, and the like are used to secure the dispersibility with a polymer matrix on the shell layer and to secure an additional protective function of the core layer.

The ligand is a compound that can bear a non-covalent electron pair to form a coordination bond, and has a functional group such as a carboxylic acid functional group, a thiol functional group, a functional group including phosphorus, and an amine or an ammonium salt functional group.

However, such a conventional quantum dot ligand can bear a non-covalent electron pair to form a coordination bond with the quantum dot particle of the metal, but since it is susceptible to storage stability to be easily oxidized by moisture and oxygen when exposed to air, there is a situation where the needs of this field for preventing oxidation of the quantum dot particle and thus preventing decrease in performance of the quantum dot are not met. In addition, there is also a disadvantage of rapidly lowering the quantum yield (QY) of the quantum dot particle.

PRIOR ART DOCUMENTS

Patent Document

European Patent Application Laid-open No. EP 3 221 421 A

DISCLOSURE

Technical Problem

As a result of making strenuous efforts to solve the above problems of the prior art, the present inventors found that an ionic liquid can form an ionic bond with a shell of a quantum dot particle, and in this case, the yield, lifespan, dispersibility, and manufacturing efficiency of the quantum dot were remarkably improved, and has completed the present invention.

Therefore, it is an object of the present invention to provide a quantum dot in which an ionic liquid is ion-bonded, that can improve the yield, lifespan, dispersibility, and manufacturing efficiency of the quantum dot, and a method of preparing the same.

Technical Solution

In order to achieve the above object, the present invention provides a quantum dot particle in which an ionic liquid is ion-bonded, characterized in that the quantum dot particle comprises:

a quantum dot having a core/shell nanostructure; and an ionic liquid compound represented by following Chemical Formula 1, bonded to the surface of the quantum dot, wherein the quantum dot and the ionic liquid compound form an ionic bond:

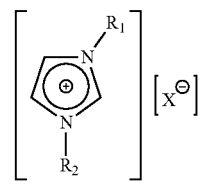

[Chemical Formula 1]

wherein, $R_1$ and $R_2$ are each independently a branched or unbranched hydrocarbon group having 1 to 22 carbon atoms, and $X^-$ is a monovalent anion, wherein the hydrocarbon group includes a saturated or unsaturated group and may include one or more hetero atoms.

In addition, the present invention provides a quantum dot particle in which an ionic liquid is ion-bonded, characterized in that the quantum dot particle comprises:

a quantum dot having a core/shell nanostructure; and an ionic liquid compound represented by following Chemical Formula 1, bonded to the surface of the quantum dot;

wherein the quantum dot and the ionic liquid compound form an ionic bond;

wherein the core of the quantum dot includes elements In and P, and the shell includes one or more elements selected from Zn, Se, and S; and wherein the initial relative quantum yield QY is 85% or more, a photoluminescence spectrum has a full width at half maximum of 50 nm or less, and the quantum yield QY after being left at room temperature of 25° C. for 7 days is 70% or more:

[Chemical Formula 1]

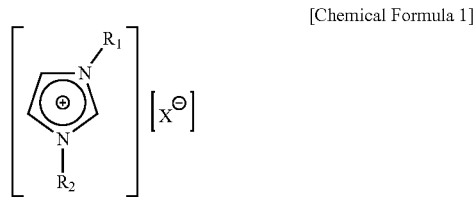

wherein, $R_1$ and $R_2$ are each independently a branched or unbranched hydrocarbon group having 1 to 22 carbon atoms, and $X^-$ is a monovalent anion, wherein the hydrocarbon group includes a saturated or unsaturated group and may include one or more hetero atoms.

In addition, the present invention provides a method of preparing a quantum dot particle in which an ionic liquid is ion-bonded, wherein the method comprises the steps of:

(a) reacting a quantum dot having a core/shell nanostructure and an ionic liquid compound represented by following Chemical Formula 1 to form an ionic bond; and (b) recovering the quantum dot in which the ionic bond is formed in step (a):

[Chemical Formula 1]

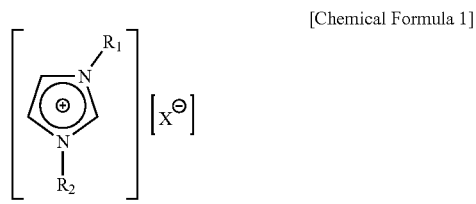

wherein, $R_1$ and $R_2$ are each independently a branched or unbranched hydrocarbon group having 1 to 22 carbon atoms, and $X^-$ is a monovalent anion, wherein the hydrocarbon group includes a saturated or unsaturated group and may include one or more hetero atoms.

Advantageous Effects

The quantum dot particle in which the ionic liquid is ion-bonded according to the present invention provides an effect of remarkably improving the yield of the quantum dot particle since the ionic liquid is effectively introduced into the quantum dot particle to minimize the quantum dot particle lost during purification, and provides effects of extending the lifespan of the quantum dot particle and improving the dispersibility of the quantum dot particle.

The method of preparing the quantum dot in which the ionic liquid is ion-bonded according to the present invention makes it possible to prepare the quantum dot efficiently by a simple method, and thus provides an effect of remarkably improving the manufacturing efficiency of the quantum dot.

BRIEF DESCRIPTION OF DRAWINGS

FIG. 1 is a drawing schematically showing the form of the quantum dot particle of the present invention.

FIG. 2 is a $^1$H-NMR spectrum of 1-butyl-3-methylimidazolium tetrafluoroborate which is an ionic liquid prepared in Preparation Example 1 of the present invention.

FIG. 3 is a photoluminescence spectrum by day when the quantum dot particle prepared in Example 1 of the present invention is stored at room temperature in air.

FIG. 4 is a photoluminescence spectrum by day when the quantum dot particle prepared in Comparative Example 1 in the present invention is stored at room temperature in air.

FIG. 5 is a graph showing changes in the photoluminescence quantum yield (PL QY) when the quantum dot particles of Example 1 of the present invention and Comparative Example 1 are stored at room temperature in air.

BEST MODE

Hereinafter, the present invention will be described in detail.

In the quantum dot of the core-shell structure, the shell serves to protect an electron and a hole of the core from the outside, but the core and the shell may be oxidized by the external environment to reduce the quantum efficiency. Therefore, a shell process to coat an inorganic shell of ZnS or ZnSSe as an outer layer is added to protect the core (for example, InP), or a method of binding a ligand is used to secure the dispersibility with a polymer matrix on the shell layer and to secure an additional protective function of the core layer.

However, despite the method of introducing the shell layer and the ligand, there is a situation where the needs of this field for preventing oxidation of the quantum dot particle by moisture or oxygen in air and thus preventing decrease in performance of the quantum dot are not sufficiently met. In addition, in the case of the ligand, since there is a disadvantage that the quantum yield (QY) of the quantum dot particle is also rapidly lowered, there is a need for improvement thereof.

The present invention suggests an ionic liquid which is ion-bonded to a quantum dot as a ligand binding to a quantum dot particle.

The ionic liquid is generally a ionic salt which is present as a liquid at 100° C. or less, and is a special liquid which has excellent ability to dissolve organic and inorganic matter and is thermally, chemically and physically stable, and thus has little vapor pressure and maintains a liquid phase even in vacuum. Such a ionic liquid are used as a solvent for the production of a nanoparticle due to its properties such as non-flammability, non-volatility, and thermal stability.

The present inventors found a structure of an ionic liquid capable of ion bonding with a shell of a nanoparticle, particularly a quantum dot particle, not an ionic liquid used as a solvent as described above, and has completed the present invention. The ionic liquid takes a form in which an anion (for example, tetrafluoroborate anion) of the ionic liquid and the quantum dot particle are bonded, not a way in which a non-covalent electron pair is coordinated to the quantum dot particle. In the case of the quantum dot particle including the ion-bonded ionic liquid as described above as a ligand, the effects of greatly improving the yield and remarkably extending the lifespan are provided.

The present invention relates to a quantum dot particle in which an ionic liquid is ion-bonded, characterized in that the quantum dot particle comprises a quantum dot having a core/shell nanostructure; and an ionic liquid compound represented by following Chemical Formula 1, bonded to the surface of the quantum dot, wherein the quantum dot and the ionic liquid compound form an ionic bond:

[Chemical Formula 1]

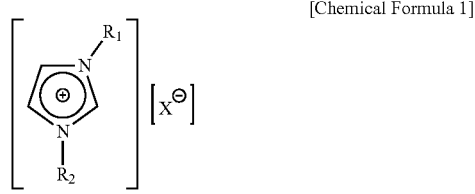

wherein, $R_1$ and $R_2$ are each independently a branched or unbranched hydrocarbon group having 1 to 22 carbon atoms, and $X^-$ is a monovalent anion, wherein the hydrocarbon group includes a saturated or unsaturated group and may include one or more hetero atoms.

In Chemical Formula 1 above, it is more preferable that $R_1$ is a branched or unbranched alkyl group having 1 to 8 carbon atoms, $R_2$ has or does not have an unsaturated group having 1 to 12 carbon atoms, and is a branched or unbranched hydrocarbon group, and $X^-$ is a monovalent anion.

In one embodiment of the present invention, the quantum dot particle may be used, wherein the core of the quantum dot includes Groups III-V compounds, and the shell is doped with one or more selected from the group consisting of aluminum, silicon, titanium, magnesium, and zinc.

In one embodiment of the present invention, the core may include one or more selected from the group consisting of GaN, GaP, GaAs, GaSb, AlN, Alp, AlAs, AlSb, InN, InP, InAs, InSb, or a mixture thereof; GaNP, GaNAs, GaNSb, GaPAs, GaPSb, AlNP, AlNAs, AlNSb, AlPAs AlPSb, InNP, InNAs, InNSb, InPAs, InPSb, or mixtures thereof; and GaAlNAs, GaAlNSb, GaAlPAs, GaAlPSb, GaInNP, GaIn-NAs, GaInNSb, GaInPAs, GaInPSb, GaAlNP, InAlNP, InAl-NAs, InAlNSb, InAlPAs, InAlPSb, or mixtures thereof.

In one embodiment of the present invention, the core may include elements In and P, and the shell may include one or more elements selected from Zn, Se, and S; and In one embodiment of the present invention, $X^-$ in the ionic liquid of Chemical Formula 1 above may be $Br^-$, $Cl^-$, $ClO_4^-$, $NO_3^-$, $CH_3SO_4^-$, $CH_3COO^-$, $BF_4^-$, $PF_6^-$, $CH_3COO^-$, $(CF_3SO_2)_2N^-$, or the like. Among the anions, tetrafluoroborate ($BF_4O^-$) may be preferably used since it can effectively ion-bond with the surface of the quantum dot.

In one embodiment of the present invention, it may be preferable that $R_1$ and $R_2$ in Chemical Formula 1 above do not include a coordinating group. This is because, when a coordinating group is included in $R_1$ and $R_2$, the ionic bond of the ionic liquid to the quantum dot may be disturbed.

In one embodiment of the present invention, the ionic liquid of Chemical Formula 1 above may be one or more selected from the group consisting of 1-ethyl-3-methylimidazolium tetrafluoroborate, 1-propyl-3-methylimidazolium tetrafluoroborate, 1-butyl-3-methylimidazolium tetrafluoroborate, 1-heptyl-3-methylimidazolium tetrafluoroborate, 1-hexyl-3-methylimidazolium tetrafluoroborate, 1-allyl-3-methylimidazolium tetrafluoroborate, 1-(2-butenyl)-3-meth-ylimidazolium tetrafluoroborate, 1-(2-pentenyl)-3-methylimidazolium tetrafluoroborate, 1,3-diethylimidazolium tetrafluoroborate, 1-propyl-3-ethylimidazolium tetrafluoroborate, 1-butyl-3-ethylimidazolium tetrafluoroborate, 1-hexyl-3-ethylimidazolium tetrafluoroborate, 1-allyl-3-ethylimidazolium tetrafluoroborate, 1-(2-butenyl)-3-ethylimidazolium tetrafluoroborate, 1-(2-pentenyl)-3-ethylimidazolium tetrafluoroborate, and the like.

In one embodiment of the present invention, the ionic liquid of Chemical Formula 1 above may be compounds represented by following Chemical Formulas 2 to 5:

[Chemical Formula 2]

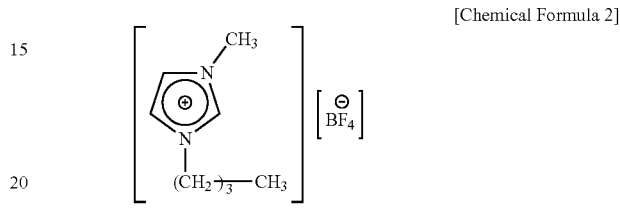

[Chemical Formula 3]

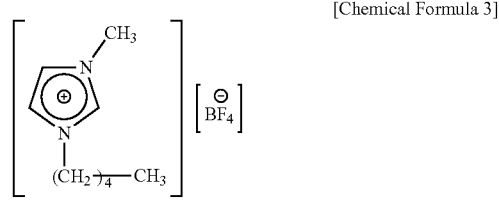

[Chemical Formula 4]

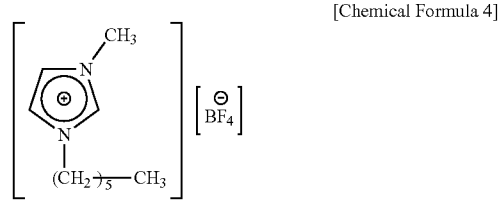

[Chemical Formula 5]

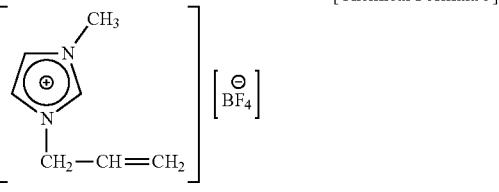

In one embodiment of the present invention, the ionic liquid of Chemical Formula 1 above may be prepared by obtaining a compound in a salt form by reaction of an imidazole derivative and an alkyl halide compound, and exchanging it with an $X^-$ anion.

In one embodiment of the present invention, the quantum dot particle may further include a ligand coordinated to the surface of the particle. Such a form may be a form in which a conventional ligand known in the art is bound to the surface of the quantum dot particle by coordination bond, or the like, and the ionic liquid ligand of the present invention is located by ion bond on the ligand end or between the ligands. The ligand to be coordinated includes ligands known in the art including a functional group such as a carboxylic acid functional group, a thiol functional group, a functional group including phosphorus, and an amine or ammonium salt functional group.

In one embodiment of the present invention, the quantum dot of the present invention may have an initial relative quantum yield QY of 85% or more, and a relative quantum yield QY after being left at room temperature of 25° C. for 7 days of 70% or more.

In addition, the quantum dot of the present invention may have a particle yield after the introduction of the ionic liquid into the quantum dot of 1.80 g or more per 100 mL of the quantum dot stock solution before the introduction of the ionic liquid.

Such effects appear very remarkable compared to the prior art.

The present invention relates to a quantum dot particle in which an ionic liquid is ion-bonded, characterized in that the quantum dot particle comprises:

a quantum dot having a core/shell nanostructure; and an ionic liquid compound represented by following Chemical Formula 1, bonded to the surface of the quantum dot, wherein the quantum dot and the ionic liquid compound form an ionic bond;

wherein the core of the quantum dot includes elements In and P, and the shell includes one or more elements selected from Zn, Se, and S; and wherein the initial relative quantum yield QY is 85% or more, a photoluminescence spectrum has a full width at half maximum of 50 nm or less, and the quantum yield QY after being left at room temperature of 25° C. for 7 days is 70% or more:

[Chemical Formula 1]

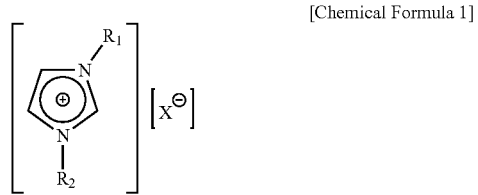

wherein, $R_1$, $R_2$, and X are the same as defined above.

In addition, the present invention relates to a method of preparing a quantum dot particle, wherein the method comprises the steps of:

(a) reacting a quantum dot having a core/shell nanostructure and an ionic liquid compound represented by following Chemical Formula 1 to form an ionic bond; and (b) recovering the quantum dot in which the ionic bond is formed in step (a):

[Chemical Formula 1]

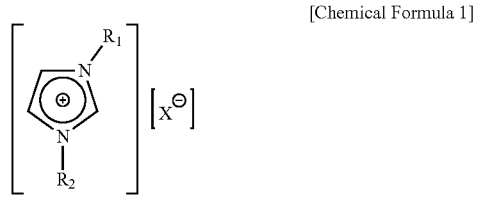

wherein, $R_1$, $R_2$, and X are the same as defined above.

In the preparation method, the method proceeding the reaction at a temperature of 50 to 200° C., preferably 80 to 150° C. for 3 to 24 hours, preferably 3 to 7 hours may be used.

In the preparation method, the quantum dot having the core/shell nanostructure may participate in the reaction in a state included in the reaction solution used in the preparation of the quantum dot. The quantum dot having the core/shell nanostructure may be prepared by a method known in the art.

In the preparation method, the step of recovering the quantum dot in which the ionic bond is formed may be performed by a conventional method known in the art.

Hereinafter, the quantum dot of the present invention will be described in more detail.

[Quantum Dot Composition]

Conventionally, the optical properties of the quantum dot particle may vary depending on its size, and the quantum dot may be substantially homogeneous in terms of material properties, but in certain embodiments, may be heterogeneous. The optical properties of the quantum dot may adjust a nanocrystal size by its particle size, chemistry, or surface composition to determine the range of photoelectron emission in the entire optical spectrum. In the quantum dot of the core/shell structure, the band gap of the semiconductor nanocrystal of the shell may have a larger energy band gap than the semiconductor nanocrystal of the core, but is not limited thereto. The band gap of the semiconductor nanocrystal of the shell may have a smaller energy band gap than the semiconductor nanocrystal of the core. In the case of a multilayer shell, the outermost layer may have a larger energy band gap than the semiconductor nanocrystal of the core and other layers of the shell.

In the multilayer shell, the band gap of the semiconductor nanocrystal of each layer may be appropriately selected to efficiently exhibit the quantum confinement effects. The semiconductor nanocrystal particle may have a particle diameter (diameter calculated from the two-dimensional area of the electron micrograph of the particle, if not spherical) of about 1 nm to about 100 nm. The quantum dot particle may have a particle size of 1 nm to 50 nm, preferably 2 nm to 35 nm, even more preferably 5 nm to 15 nm. The size of the quantum dot may be 1 nm or more, 2 nm or more, 3 nm or more, 4 nm or more, or 5 nm or more. The size of the quantum dot may be 50 nm or less, 40 nm or less, 30 nm or less, 25 nm or less, 20 nm or less, 19 nm or less, 18 nm or less, 17 nm or less, 16 nm or less, or 15 nm or less. The shape of the semiconductor nanocrystal particle is not specially limited, and may be, for example, spherical, pyramidal, multi-arm, or cubic nanotubes, nanowires, nanofibers, nanosheets, or a combination thereof, but is not limited thereto.

Referring to FIG. 2, the quantum dots according to the present examples include a core layer 10, and a shell layer 20 surrounding the core layer 10. In this case, the shell layer 20 is doped with a metal material. The doped metal material may include at least one of aluminum, silicon, titanium, magnesium, and zinc. The metal material doped at the outermost portion of the shell layer 20 may have an oxide form. The core layer 10 includes Groups III-V compounds, and Group III-V compounds may be selected from the group consisting of binary compounds selected from the group consisting of GaN, GaP, GaAs, GaSb, AlN, Alp, AlAs, AlSb,InN, InP, InAs, InSb, and a mixture thereof; ternary compound selected from the group consisting of GaNP, GaNAs, GaNSb,GaPAs, GaPSb, AlNP, AlNAs, AlNSb, AlPAs, AlPSb, InNP, InNAs, InNSb, InPAs, InPSb, and mixtures thereof; and quaternary compounds selected from the group consisting of GaAlNAs, GaAlNSb, GaAlPAs, GaAlPSb, GaInNP, GaInNAs, GaInNSb,GaInPAs, GaInPSb, GaAlNP, InAlNP, InAlNAs, InAlNSb, InAlPAs, InAlPSb, and mixtures thereof.

The shell layer 20 includes at least one of Zn, Se, and S, and by way of example, the shell layer 20 may be ZnSeS, ZnSe, or ZnS.

The quantum dot particle is commercially available or may be synthesized by any method. The quantum dot may be synthesized through a chemical wet method. In the chemical wet method, a metal and a nonmetallic precursor are reacted in an organic solvent to grow a crystal particle, and the growth of the crystal may be controlled by coordinating the organic solvent and/or an organic ligand to the surface of the quantum dot particle.

The synthesized quantum dot may be recovered by centrifugation on an excess non-solvent in the reaction solution containing the same. Examples of the non-solvent include, but are not limited to, acetone, ethanol, methanol, and the like.

The light emission wavelength of the quantum dot is not specifically limited, and may be appropriately selected. The photoluminescence peak wavelength of the quantum dot may exist from the ultraviolet region to the near infrared region, and preferably the maximum photoluminescence peak wavelength may be present in the range of 420 to 700 nm, but is not limited thereto. The light emission wavelength of the quantum dot may have a quantum yield of about 10% or more, for example, about 20% or more, about 30% or more, about 40% or more, about 50% or more, about 60% or more, about 70% or more, about 80% or more, and about 85 or more, and it is preferable to initially secure a quantum yield of 85% or more, and the quantum yield after being stored in the air for 7 days must be preferably 70% or more, more preferably 75% or more to secure the storage stability, so that it is possible to secure a stable properties.

[Ionic Liquid as Quantum Dot-Ion-Binding Ligand]

The present invention provides an ionic liquid ligand for binding to the quantum dot, and related materials. An ionic liquid, which is a quantum dot binding ligand of the present invention, have an anion bonded to a shell of a quantum dot by an ion bond to improve the stability of a ligand-quantum dot complex.

In relation to the ionic liquid, a salt melted at room temperature is also referred to as an ionic liquid, and a salt with a melting point of 100° C. or less is also referred to as an ionic liquid, and although somewhat different in concept, a salt that is a liquid at room temperature is defined as an ionic liquid in the present invention. Since the constituent ions of the ionic liquid are organic substances, various derivatives may be obtained.

Although it is less likely to become a liquid phase even if various kinds of ions are properly combined, following known techniques suggest possible structures that may be prepared as a liquid salt by appropriate design:

See J. S. Wilkes, M. J. Zaworotko, J. Chem. Soc., Chem. Commun.,965(1992);

"Ionic Liquids—The Front and Future of Material Development," CMC Press (2003);

Ionic liquids in synthesis; P. Wassersheid, T. Welton, Eds.Wiley VCH: Weinheim, 2003; Green Industrial Applications of Ionic Liquida; R. D. Rogers, K. R. Seddon, Eds. Kluwer: Dordrecht, T. Welton, Chem. Rev. 1999, 99, 2071 (2003);

B. Jastorff et. al., Green Chem., in press, (2003);

C. J. Bradaric et. al. Green Chem., in press, (2003).

As a method of preparing an ionic liquid, a synthesis method using a heterocyclic compound is most known. Although many ionic liquids have been designed so far, it will be described in the present invention with a cation based on a heteroaromatic ring of imidazolium, the effect of which is confirmed as a ligand binding to the quantum dot. Although different properties are shown depending on the kinds of conjugate anion, salts composed of heterocyclic cations, especially imidazolium cations exhibit low melting points.

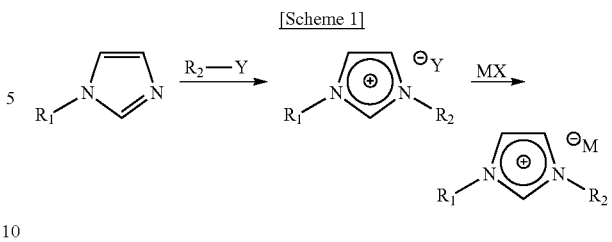

[Scheme 1]

$R_1$ and $R_2$ are the same as described above.

$R_2$—Y is an alkyl halide compound, wherein Y is a halogen element, such as F, Cl, Br, or I, X is ammonium, lithium, sodium, or potassium, M may be $BF_4^-$, $PF_6^-$, $CF_3SO_3^-$, $CF_3SO_3^-$, $(CF_3SO_3)_2N^-$, $C_3F_7COO^-$, or the like.

The ionic liquid is obtained by obtaining a heteroaromatic ring of imidazolium in salt form by quaternization reaction of an amine using an imidazole derivative and an alkyl halide, and exchanging it with an appropriate anion.

As the imidazole derivative, 1-methylimidazole, 1-ethylimidazole, 1-propylimidazole, 1-butylimidazole, 1-pentylimidazole, 1-hexylimidazole, 1-benzylimidazole, 1-cyanoethyl-imidazole, 1-vinylimidazole, 1,2-dimethylimidazole, 2-bromo-4-nitroimidazole, 2-chloro-4-nitroimidazole, 2-ethyl-4-methylimidazole, 2-ethylimidazole, 2-heptadecylimidazole, 2-isopropylimidazole, 2-mercaptobenzylimidazole, 2-isopropylimidazole, 2-methyl-5-nitroimidazole, 2-methyl-5-nitroimidazole, 2-methylimidazole, 2-phenyl-4,5-dihydroxymethylimidazole, 2-phenylimidazole, 2-propylimidazole, and the like may be used, and it may be preferable to use 1-methylimidazole, 1-ethylimidazole, 1-propylimidazole, and 1-butylimidazole, it is more preferably advantageous to apply 1-methylimidazole and 1-ethylimidazole to the present invention.

As the alkyl halide, any compound may be used as long as it is a halogen compound, for example, a compound in which elements such as fluorine, chlorine, bromine, and iodine are introduced into the alkyl chain, and compounds in which chlorine and bromine are introduced may be preferably used in consideration of the price or reactivity of the compound.

The alkyl may or may not contain an unsaturated group. The alkyl may have a straight or branched structure. In addition, the alkyl may include a hetero atom.

As the alkyl halide, any of a primary alkyl halide, a secondary alkyl halide, a tertiary alkyl halide may be used, but it is preferable to use a primary alkyl halide in consideration of reactivity or reaction yield.

As the primary alkyl halide, alkyl chloride compounds, such as 1-chloroethyl, 1-chloropropyl, 1-chloroisopropyl, 1-chlorobutyl, 1-chloroisobutyl, 1-chloro-tert-butyl, 1-chloropentyl, 1-chlorohexyl, 1-chloroheptyl, 1-chlorooctyl, 1-chlorononyl, 1-chlorodecyl, 1-chloroundecyl, 1-chlorododecyl, 1-chloro-tridecyl, allyl chloride, 1-chloro-2-butene, 1-chloro-2-pentene, and 1-chloro-2-hexene; and alkyl bromide compounds, such as 1-bromoethyl, 1-bromopropyl, 1-bromoisopropyl, 1-bromobutyl, 1-bromoisobutyl, 1-bromo-tert-butyl, 1-bromopentyl, 1-bromohexyl, 1-bromoheptyl, 1-bromooctyl, 1-bromononyl, 1-bromodecyl, 1-bromoundecyl, 1-bromododecyl, 1-bromo-tridecyl, allyl bromide, 1-bromo-2-butene, 1-bromo-2-pentene, and 1-bromo-2-hexene may be applied, and preferably 1-chloropropyl, 1-chlorobutyl, 1-chloropentyl, 1-chlorohexyl, allyl chloride, 1-chloro-2-butene, 1-chloro-2-pentene, 1-bromopropyl, 1-bromobutyl, 1-bromopentyl, 1-bromohexyl, allyl bromide, 1-bromo-2-butene, 1-bromo-2-pentene, and the like may be used.

The heteroaromatic ring of imidazolium in salt form may prepared by quaternization reaction of an amine using the imidazole derivative and the alkyl halide. The desired ionic liquid may be prepared by reacting the heteroaromatic ring of the imidazolium with MX in acid or salt form consisting of the anionic structure (M$^-$) of the ionic liquid compound. X is a basic ion and may be selected from the group of ammonium, lithium, sodium, and potassium, M is tetrafluoroborate, pyridinium hexafluorophosphate, pyridinium trifluoromethanesulphonate, pyridinium bis(trifluoromethanesulfonyl)imide, pyridinium tetrafluoroborate, acetate anion, methanesulfonate, trifluorocarboxylato, perfluorocarboxylato, and the like may be used, but among these, tetrafluoroborate (BF$_4^-$) may be preferably used since it may effectively ion-bind to the surface of the quantum dot.

In the preparation of the ionic liquid, the heteroaromatic ring of the imidazolium in salt form may be prepared by quaternization reaction using 1 to 10 moles, preferably 2 to 8 moles of alkyl halide, based on 1 mole of the imidazole derivative.

A solvent may be used to facilitate the reaction. The solvent may be used without limiting as long as it is a solvent having a polarity, and preferably water, methanol, ethanol, acetonitrile, acetone, and the like may be used alone or in combination. The reaction may be performed at 40° C. to 90° C., preferably 50° C. to 80° C., for 12 hours to 150 hours, preferably for 24 hours to 120 hours. The alkyl halide, which is used in excess, may be removed by dissolving the synthesized heteroaromatic ring of the imidazolium in water and extracting it using a halogenated solvent such as methylene chloride, methylene dichloride, methyl chloroform, and carbon tetrachloride, which are organic solvents.

MX in acid or salt form consisting of the anionic structure (M$^-$) may be subjected to an anion exchange reaction with the heteroaromatic ring of the imidazolium at a molar ratio of 1:1 to prepare an ionic liquid.

A solvent may be used to facilitate the reaction during the preparation of the ionic liquid. Preferably, as the solvent capable of well dissolving the heteroaromatic ring of the imidazolium and the ionic liquid, an ester-based solvent such as methyl acetate, ethyl acetate, propyl acetate, isopropyl acetate, butyl acetate, isobutyl acetate, pentyl acetate, and acetate isopentyl; a ketone-based solvent such as acetone, methyl ethyl ketone, methyl butyl ketone, and methyl isobutyl ketone; an aromatic hydrocarbon solvent such as benzene, toluene, and xylene; and the like may be used alone or in combination.

The reaction of the ionic liquid may be carried out at a reaction temperature of 10° C. to 60° C., preferably 15° C. to 40° C., for 12 hours to 150 hours, preferably 24 hours to 120 hours.

Upon completion of the reaction, salts are produced as a white powder (XY) in addition to the ionic liquid produced through the anion exchange reaction. The resulting white powder may be removed by filtration, and the solvent used may be removed via vacuum distillation to obtain a pure ionic liquid.

The ionic liquid compound which may be preferably used as the ionic liquid and the ligand for the surface of the quantum dot particle may include 1-ethyl-3-methylimidazolium tetrafluoroborate, 1-propyl-3-methylimidazolium tetrafluoroborate, 1-butyl-3-methylimidazolium tetrafluoroborate, 1-heptyl-3-methylimidazolium tetrafluoroborate, 1-hexyl-3-methylimidazolium tetrafluoroborate, 1-allyl-3-methylimidazolium tetrafluoroborate, 1-(2-butenyl)-3-methylimidazolium tetrafluoroborate, 1-(2-pentenyl)-3-methylimidazolium tetrafluoroborate, 1,3-diethylimidazolium tetrafluoroborate, 1-propyl-3-ethylimidazolium tetrafluoroborate, 1-butyl-3-ethylimidazolium tetrafluoroborate, 1-hexyl-3-ethylimidazolium tetrafluoroborate, 1-allyl-3-ethylimidazolium tetrafluoroborate, 1-(2-butenyl)-3-ethylimidazolium tetrafluoroborate, 1-(2-pentenyl)-3-ethylimidazolium tetrafluoroborate, and the like.

[Preparation of Quantum Dot Particle]

The high-efficiency light-emitting quantum dot of the present invention, in particular, a nanostructured high-efficiency light-emitting quantum dot particle having an InP core may be prepared by the methods of the preparation examples of the present invention, which are known in the art, including U.S. Pat. Nos. 7,557,028, 8,062,967, and 7,645,397, U.S. Patent Application Laying-Open No. US 2010/0276638, and the like.

The In-containing precursor may be the same as or different from the In-containing precursor(s) used during InP nanostructure synthesis. The In-containing precursor may include trichloroindium, chloroindium oxalate, indium oxide, indium phenoxy, and trialkyl, trialkenyl, and trialkynyl indium compounds, and the like, especially, compounds used in the art as a precursor for nanostructure synthesis may be used, but are not limited thereto. Preferably, the In-containing precursor may include an indium carboxylate compound, for example, indium acetate, indium halide, and the like, and preferably indium acetate may be used. The indium acetate must be surface modified in a suitable solvent in order to control the particle size, and in this case, a saturated or unsaturated aliphatic carboxylate compound of C5 to C18 may be used for surface modification. The saturated or unsaturated aliphatic carboxylate compound include hexanoic acid, pentanoic acid, octanoic acid, nonanoic acid, decanoic acid, dodecanoic acid, lauric acid, tridecyl acid, myristic acid, pentadecyl acid, pamic acid, margaric acid, stearic acid, oleic acid, myristoleic acid, palmitoleic acid, saphenic acid, and the like, and preferably lauric acid, tridecyl acid, myristic acid, pentadecyl acid, oleic acid, and the like may be used.

As the appropriate solvent, those commonly used in the nanostructure synthesis, in particular, non-coordinating solvents may be applied, and, for example, 1-octadecene, 1-decene, 1-dodecene, tetradecane, and the like may be used.

In the preparation of the In-containing precursor, a method of preparing a core of an InP quantum dot is provided, the method comprising: a first step of modifying the surface of the In-precursor by mixing indium acetate and the saturated or unsaturated aliphatic carboxylate compound and heating the mixture to 80 to 120° C. in the solvent; a second step of dissolving tris(trimethylsilyl)phosphine, which is a precursor for preparing an InP-based quantum dot, in trioctyl phosphine; a third step of preparing an InP quantum dot by heating the solution prepared in the first step to 200° C. to 300° C., injecting the solution prepared in the second step thereto, and reacting them; a fourth step of cooling a solution including InP quantum dot in the third step; and a fifth step of precipitating and purifying the InP quantum dot from the solution cooled in the fourth step.

The molar ratio of indium acetate and the saturated or unsaturated aliphatic carboxylate compound in the first step may be 1:2 to 1:5.

In the third step, the core of the InP quantum dot may be prepared by heating the solution prepared in the first step to 100° C. to 200° C., instead of heating the solution prepared in the first step to 200° C. to 300° C., and reacting the solution for 30 minutes to 2 hours, and then, injecting the solution prepared in the second step thereto and further heating the solution at 200° C. to 300° C. for 30 minutes to 2 hours.

In the third step, the core of the InP quantum dot may be prepared by heating the solution prepared in the first step to 250° C. to 300° C., instead of heating the solution prepared in the first step to 200° C. to 300° C., and then, injecting the solution prepared in the second step thereto and reacting the solution.

A core including an InP quantum dot prepared by reaction of the tris(trimethylsilyl)phosphine, which is a precursor for preparing an InP-based quantum dot, and an indium (In) precursor; and a shell surrounding the core optionally comprises more than one layer. Suitable precursors for shell formation are known. For example, a suitable precursor for a $ZnS_xSe_{1-x}$ (wherein $0<x<1$) shell formation includes diethyl zinc, zinc carboxylate, such as zinc stearate or zinc hexanoate, bis(trimethylsilyl)selenide, elements such as selenium (dissolved in tributylphosphine), hexamethyldisylthiane, and organic thiol, such 1-dodecanethiol, tert-dodecylmercaptan, or 1-octanethiol. The thickness of the shell layer is optionally controlled by controlling the amount of precursor(s) provided. For a given layer, one or more precursors are optionally provided in an amount when the growth reaction is substantially completed, and the layer has a predetermined thickness. If more than one different precursor is provided, the amount of each precursor may be limited, or any one of the precursors may be provided while limiting the amount in which the other is provided in excess. Suitable amounts of precursors for various manufactures with the desired shell thickness may be readily calculated. For example, the InP core may be dispersed in a solvent after its synthesis and purification, and its concentration may be calculated by UV/Vis spectroscopy using Beer-Lambert law. That is, the absorption coefficient may be obtained from bulk InP and may be expressed as the optical density of $1^{st}$ excitonic absorption of InP dispersed in a solvent.

In the present invention, an $InP/ZnS_xSe_{1-x}$ quantum dot including a shell including $ZnS_xSe_{1-x}$ (wherein $0<x<1$) is provided.

A method of preparing an InP/ZnS quantum dot is provided, the method comprising: a sixth step of mixing zinc acetate and the saturated or unsaturated aliphatic carboxylate compound in the solvent and heating it to 80 to 120° C.; a seventh step of preparing a solution including sulfur or selenium in trialkylphosphine, and then stirring it; an eighth step of mixing the InP quantum dot core purified in the fifth step, the solvent, and the solution prepared in the sixth step, and then heating them to 80 to 120° C.; and a ninth step of mixing the solution prepared in the eighth step with the solution prepared in the seventh step, heating them to 200° C. to 300° C., and reacting them to prepare an $InP/ZnS_xSe_{1-x}$ quantum dot which includes the InP quantum dot as a core and includes $ZnS_xSe_{1-x}$ (wherein $0<x<1$) shell surrounding the core.

[Preparation of Quantum Dot Particle in which Ionic Liquid is Ion-Bonded]

The quantum dot particle is optionally mixed with a matrix (for example, an organic polymer, silicon-containing polymer, inorganic, glassy, and/or other matrix). The thus mixed quantum dot particle may be applied to, for example, an LED light-emitting element, a backlight unit, a downlight, or another display or lighting unit, or an optical filter. The exemplified matrices and elements are known in the art, and the quantum dot particle having a nanostructure may include a ligand layer to secure dispersibility with the matrix and preserve the lifespan of the quantum dot particle. The saturated or unsaturated aliphatic carboxylate compounds used during the shell preparation process partially serve as a ligand but are insufficient. For this reason, in order to increase the dispersibility with the matrix and extend the lifespan of the quantum dot particle, a ligand exchange reaction with the ionic liquid is further carried out in the present invention. When the ligand is exchanged with the ionic liquid, in addition to the advantages mentioned above, high yields may be ensured. This means that the ionic liquid is effectively introduced into the quantum dot particle, thereby providing the advantage capable of minimizing the quantum dot particle lost during purification.

The introduction of the ligand to the ionic liquid (the ligand exchange of any carboxylic acid type aliphatic compound is also the same) may be achieved by mixing the ionic liquid in $InP/ZnS_xSe_{1-x}$ quantum dot solution of the ninth step of the shell preparation process, and preferably proceeding the reaction at a temperature of 50 to 200° C., preferably 80 to 150° C., for 3 to 24 hours.

After the ligand exchange reaction by the ionic liquid is completed as described above, the quantum dot particle stable to an organic solvent can be prepared, by adding excess ethanol to the mixture and centrifuging it to remove excess organic matter present in the quantum dot, and discharging the centrifuged supernatant and drying the centrifuged precipitate, and then dispersing the dried precipitate in the non-polar solvent, for example, hexane, heptane, octane, benzene, toluene, xylene, and the like.

On the other hand, in the case of the ionic liquid in which the thiol group is introduced, the coordination bond rate by the thiol group is remarkably faster than the ligand exchange reaction by the ionic bond of the ionic liquid. That is, when there is a thiol group in the structure of the ionic liquid, the coordination bond by the thiol functional group is made much faster than the ionic bond. Therefore, when the ligand exchange reaction proceeds only with the ionic liquid into which the thiol group is introduced, the quantum dot particle in which the ionic liquid is ion-bonded cannot be prepared. Of course, when the ionic liquid into which a thiol group is introduced and a general ionic liquid capable of ion bonding are used together, a quantum dot particle including both an ionic liquid ligand coordinated by a thiol group and an ion-bonded ionic liquid ligand may be prepared.

In consideration of the ionic bond of the ionic liquid in the present invention, it may not be preferable to use an ionic liquid in which a thiol group is introduced or an ionic liquid in which an alkoxysilane (SiOR) group is introduced.

The quantum dot particle in which the ionic liquid is ion-bonded according to the present invention contains preferably 30% or more, more preferably 50% or more, even more preferably 80% or more, particularly preferably 100% of ion-bonded quantum dot particle in the total ionic liquid bonded to the quantum dot. When the ion-bonded quantum dot particle is included in less than 30%, it is difficult to sufficiently obtain effects such as improved yield of the quantum dot, extended lifespan of the quantum dot particle, and improved dispersibility of the quantum dot particle, in the preparation of quantum dot.

Hereinafter, preferred examples will be provided to help understanding the present invention, but the following examples are only for illustrating the present invention, and it will be apparent to those skilled in the art that various changes and modifications may be made within the scope and technical spirit of the present invention, and it is obvious that such changes and modifications fall within the scope of the appended claims.

Preparation Example 1

Synthesis of 1-Butyl-3-Methylimidazolium Tetrafluoroborate

In a 4-neck 500 mL jacketed reactor equipped with a mechanical stirrer, a thermometer, and a reflux cooling tube, 12.3 parts by weight (0.15 mol) of 1-methylimidazole and 61.8 parts by weight (0.45 mol) of 1-bromobutane were dissolved in 300 parts by weight of acetonitrile, and then the reaction was carried out at 80° C. for 48 hours. Thereafter, acetonitrile was removed by concentration under reduced pressure, and 200 parts by weight of ultrapure water was added thereto to completely dissolve the reactant, and then washing was performed five times with 200 parts by weight of methylene dichloride in a separatory funnel to remove unreacted 1-bromobutane. Then, distillation under reduced pressure at 100° C. was performed to prepare 26.1 g (yield 79.4%) of 1-butyl-3-methylimidazolium bromide. In a 4-neck 500 mL jacketed reactor equipped with a mechanical stirrer, a thermometer, and a reflux cooling tube, 21.9 parts by weight (0.1 mol) of 1-butyl-3-methylimidazolium bromide prepared above was dissolved in 200 parts by weight of acetone, and then 9.4 parts by weight (0.1 mol) of lithium tetrafluoroborate was added thereto and an anion substitution reaction was carried out at 20° C. for 30 hours. By-product LiBr (lithium bromide) produced through the anion substitution reaction was precipitated as a white solid powder. The solution was filtered through a celite filter, and acetone was concentrated to finally give 22.1 g (yield 97.8%) of colorless transparent 1-butyl-3-methylimidazolium tetrafluoroborate.

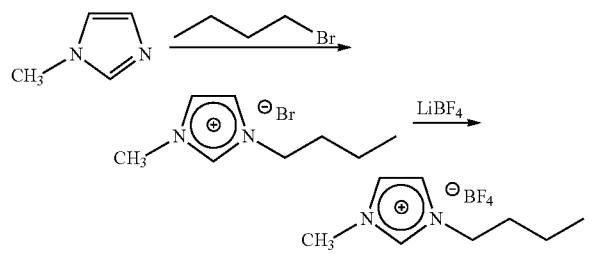

$^1$H-NMR (270 MHz, Chloroform-d) d: 8.8 (1H, s, NCHN), 7.4 (1H, t, CH$_3$NCHCHN), 7.3 (1H, t, CH$_3$NCHCHN), 4.1 (2H, t, NCH$_2$(CH$_2$)2CH$_3$), 3.8 (3H, s, NCH$_3$), 1.7 (2H, m, NCH$_2$CH$_2$CH$_2$CH$_3$), 1.2 (2H, m, N(CH$_2$)2CH$_2$CH$_3$), 0.7 (3H, t, N(CH$_2$)$_3$CH$_3$).

Mass spectrum (FAB+ve) m/z: 139 (M–BF4)$^+$

The $^1$H-NMR spectrum of the 1-butyl-3-methylimidazolium tetrafluoroborate is shown in FIG. 1.

Preparation Example 2

Synthesis of 1-Pentyl-3-Methylimidazolium Tetrafluoroborate

In a 4-neck 500 mL jacketed reactor equipped with a mechanical stirrer, a thermometer, and a reflux cooling tube, 12.3 parts by weight (0.15 mol) of 1-methylimidazole and 70.0 parts by weight (0.45 mol) of 1-bromopentane were dissolved in 300 parts by weight of acetonitrile, and then the reaction was carried out at 80° C. for 48 hours. Thereafter, acetonitrile was removed by concentration under reduced pressure, and 200 parts by weight of ultrapure water was added thereto to completely dissolve the reactant, and then washing was performed five times with 200 parts by weight of methylene dichloride in a separatory funnel to remove unreacted 1-bromopentane. Then, distillation under reduced pressure at 100° C. was performed to prepare 27.6 g (yield 78.9%) of 1-pentyl-3-methylimidazolium bromide.

In a 4-neck 500 mL jacketed reactor equipped with a mechanical stirrer, a thermometer, and a reflux cooling tube, 23.3 parts by weight (0.1 mol) of 1-pentyl-3-methylimidazolium bromide prepared above was dissolved in 200 parts by weight of acetone, and then 9.4 parts by weight (0.1 mol) of lithium tetrafluoroborate was added thereto and an anion substitution reaction was carried out at 20° C. for 30 hours. By-product LiBr (lithium bromide) produced through the anion substitution reaction was precipitated as a white solid powder. The solution was filtered through a celite filter, and acetone was concentrated to finally give 23.1 g (yield 96.3%) of colorless transparent 1-pentyl-3-methylimidazolium tetrafluoroborate.

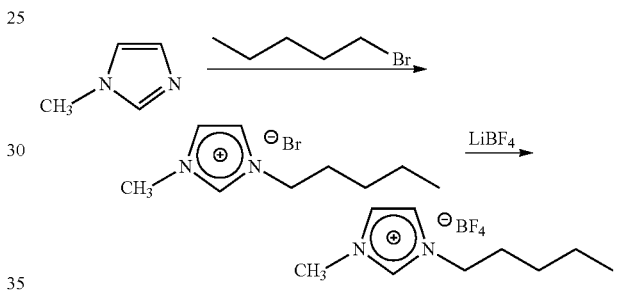

$^1$H-NMR (270 MHz, Chloroform-d) d: 8.8 (1H, s, NCHN), 7.4 (1H, t, CH$_3$NCHCHN), 7.3 (1H, t, CH$_3$NCHCHN), 4.1 (2H, t, NCH$_2$ (CH$_2$)$_3$CH$_3$), 3.8 (3H, s, NCH$_3$), 1.7 (4H, m, NCH$_2$CH$_2$CH$_2$CH$_2$CH$_3$) 1.2 (2H, m, N(CH$_2$)$_3$CH$_2$CH$_3$), 0.7 (3H, t, N(CH$_2$)$_3$CH$_3$).

Mass spectrum (FAB+ve) m/z: 153 (M–BF4)$^+$

Preparation Example 3

Synthesis of 1-Hexyl-3-Methylimidazolium Tetrafluoroborate

In a 4-neck 500 mL jacketed reactor equipped with a mechanical stirrer, a thermometer, and a reflux cooling tube, 12.3 parts by weight (0.15 mol) of 1-methylimidazole and 74.3 parts by weight (0.45 mol) of 1-bromohexane were dissolved in 300 parts by weight of acetonitrile, and then the reaction was carried out at 80° C. for 48 hours. Thereafter, acetonitrile was removed by concentration under reduced pressure, and 200 parts by weight of ultrapure water was added thereto to completely dissolve the reactant, and then washing was performed five times with 200 parts by weight of methylene dichloride in a separatory funnel to remove unreacted 1-bromohexane. Then, distillation under reduced pressure at 100° C. was performed to prepare 29.3 g (yield 79.1%) of 1-hexyl-3-methylimidazolium bromide.

In a 4-neck 500 mL jacketed reactor equipped with a mechanical stirrer, a thermometer, and a reflux cooling tube, 24.7 parts by weight (0.1 mol) of 1-hexyl-3-methylimidazolium bromide prepared above was dissolved in 200 parts by weight of acetone, and then 9.4 parts by weight (0.1 mol)

of lithium tetrafluoroborate was added thereto and an anion substitution reaction was carried out at 20° C. for 30 hours. By-product LiBr (lithium bromide) produced through the anion substitution reaction was precipitated as a white solid powder. The solution was filtered through a celite filter, and acetone was concentrated to finally give 24.5 g (yield 96.5%) of colorless transparent 1-hexyl-3-methylimidazolium tetrafluoroborate.

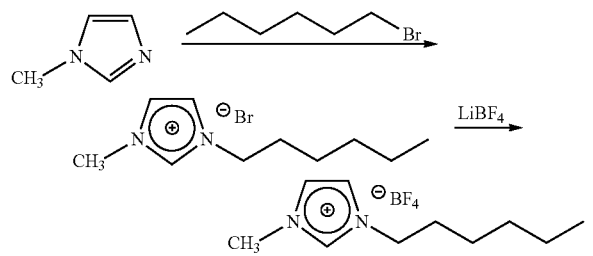

$^1$H-NMR (270 MHz, Chloroform-d) d: 8.8 (1H, s, NCHN), 7.4 (1H, t, CH$_3$NCHCHN), 7.3 (1H, t, CH$_3$NCHCHN), 4.1 (2H, t, NCH$_2$ (CH$_2$)$_4$CH$_3$), 3.8 (3H, s, NCH$_3$), 1.7 (6H, m, NCH$_2$CH$_2$CH$_2$CH$_2$CH$_2$CH$_3$) 1.2 (2H, m, N(CH$_2$) 4CH$_2$CH$_3$), 0.7 (3H, t, N(CH$_2$)$_3$CH$_3$).

Mass spectrum (FAB+ve) m/z: 167 (M−BF$_4$)$^+$

Preparation Example 4

Synthesis of 1-Allyl-3-Methylimidazolium Tetrafluoroborate

In a 4-neck 500 mL jacketed reactor equipped with a mechanical stirrer, a thermometer, and a reflux cooling tube, 12.3 parts by weight (0.15 mol) of 1-methylimidazole and 54.5 parts by weight (0.45 mol) of 1-allyl bromide were dissolved in 300 parts by weight of acetonitrile, and then the reaction was carried out at 80° C. for 48 hours. Thereafter, acetonitrile was removed by concentration under reduced pressure, and 200 parts by weight of ultrapure water was added thereto to completely dissolve the reactant, and then washing was performed five times with 200 parts by weight of methylene dichloride in a separatory funnel to remove unreacted allyl bromide. Then, distillation under reduced pressure at 100° C. was performed to prepare 23.6 g (yield 77.6%) of 1-allyl-3-methylimidazolium bromide.

In a 4-neck 500 mL jacketed reactor equipped with a mechanical stirrer, a thermometer, and a reflux cooling tube, 20.3 parts by weight (0.1 mol) of 1-allyl-3-methylimidazolium bromide prepared above was dissolved in 200 parts by weight of acetone, and then 9.4 parts by weight (0.1 mol) of lithium tetrafluoroborate was added thereto and an anion substitution reaction was carried out at 20° C. for 30 hours. By-product LiBr (lithium bromide) produced through the anion substitution reaction was precipitated as a white solid powder. The solution was filtered through a celite filter, and acetone was concentrated to finally give 20.5 g (yield 97.8%) of colorless transparent 1-allyl-3-methylimidazolium tetrafluoroborate.

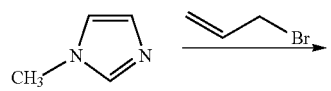

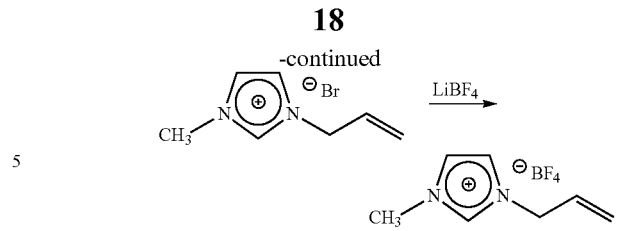

$^1$H-NMR (270 MHz, Chloroform-d) d: 8.8 (1H, s, NCHN), 7.4 (1H, t, CH$_3$NCHCHN), 7.3 (1H, t, CH$_3$NCHCHN), 6.1 (1H, t, NCH$_2$CH=CH$_2$), 5.3 (2H, m, NCH$_2$CH=CH$_2$), 5.1 (2H, t, NCH$_2$CH=CH$_2$), 3.8 (3H, s, NCH$_3$)

Mass spectrum (FAB+ve) m/z: 123 (M−BF$_4$)$^+$

Preparation Example 5

Synthesis of 1-Mercaptobutyl-3-Methylimidazolium Tetrafluoroborate

In a 4-neck 500 mL jacketed reactor equipped with a mechanical stirrer, a thermometer, and a reflux cooling tube, 12.3 parts by weight (0.15 mol) of 1-methylimidazole and 97.2 parts by weight (0.45 mol) of 1,4-dibromobutane were dissolved in 300 parts by weight of acetonitrile, and then the reaction was carried out at 80° C. for 48 hours. Thereafter, acetonitrile was removed by concentration under reduced pressure, and 200 parts by weight of ultrapure water was added thereto to completely dissolve the reactant, and then washing was performed five times with 200 parts by weight of methylene dichloride in a separatory funnel to remove unreacted 1,4-dibromobutane. Then, distillation under reduced pressure at 100° C. was performed to prepare 35.3 g (yield 79.1%) of 1-bromo-butyl-3-methylimidazolium bromide.

In a 4-neck 1000 mL jacketed reactor equipped with a mechanical stirrer, a thermometer, and a reflux cooling tube, 32.8 parts by weight (0.11 mol) of 1-bromo-butyl-3-methylimidazolium bromide was dissolved in 100 parts by weight of tetrahydrofuran, and then 12.6 parts by weight (0.11 mol) of potassium thioacetate salt was added thereto and an anion substitution reaction was carried out at 35° C. for 10 hours. 300 parts by weight of ethanol was mixed with the reaction product of which the reaction was completed, 100 parts by weight of 10% aqueous sodium hydroxide solution was added thereto, and 48% aqueous bromic acid solution was added while stirring to adjust the internal pH to be 2. The thus resulting reaction product was extracted with chloroform and dried to obtain 13.3 g (yield 43.8%) of 1-mercaptobutyl-3-methylimidazolium bromide.

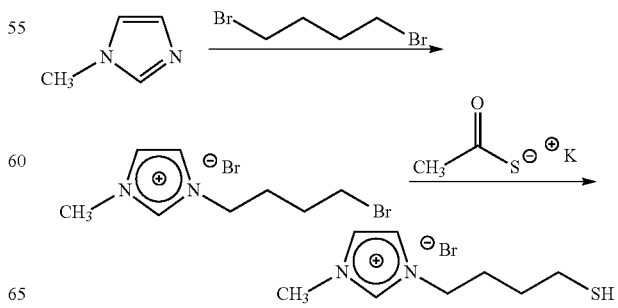

¹H-NMR (270 MHz, Chloroform-d) d: 8.8 (1H, s, NCHN), 7.4 (1H, t, CH₃NCHCHN), 7.3 (1H, t,CH₃NCHCHN), 4.1 (2H, t, NCH₂ (CH₂)₃CH₃), 3.8 (3H, s, NCH₃), 2.5 (2H, m, NCH₂CH₂CH₂CH₂CH₂SH) 1.7 (6H, m, NCH₂CH₂CH₂CH₂CH₂SH), 1.2 (H, s, N(CH₂)₃CH₂SH).

Mass spectrum (FAB+ve) m/z: 171 (M−Br)⁺

Preparation Example 6

Preparation of InP Particle (Core)

To synthesize an InP core nanoparticle, 0.05839 g (0.2 mmol) of indium acetate, 0.12019 g (0.6 mmol) of lauric acid, and 10 mL of 1-octadecene were placed in a 3-neck flask. The flask was subjected to a process of removing the volatile components at 110° C. under 100 mTorr for 30 minutes while stirring, and then the reaction was carried out while maintaining the temperature of 270° C. in a nitrogen atmosphere until the solution became transparent. 0.02435 g (0.05 mmol) of tris(trimethylsilyl)phosphine and 1 ml of trioctylphosphine were mixed, stirred, and rapidly injected into the previous flask heated to 270° C. in a nitrogen atmosphere. After reaction for 1 hour, the mixture was cooled rapidly to terminate the reaction. Then, when the temperature of the flask reached 100° C., 10 mL of toluene was injected thereto, and then transferred to a 50 mL centrifuge tube. After addition of 10 mL of ethanol, purification was repeated twice using precipitation and re-dispersion methods, and it was dispersed in 13 g of toluene to prepare a quantum dot particle dispersion of InP core, wherein optical density of 1$^{st}$ excitonic absorption was 0.3.

Preparation Example 7

Preparation of ZnS$_x$Se$_{1-x}$ Shell of InP Particle (Core)

To synthesize an InP/ZnS nanoparticle, 5.5044 g (30 mmol) of zinc acetate, 16.944 g (60 mmol) of oleic acid, and 30 mL of 1-octadecene were placed in a 3-neck flask. A mixture including a first compound dispersed by 1-octadecene produced through a process of removing the volatile components at 140° C. under 100 mTorr for 30 minutes while stirring the flask was stored at 100° C. under an inert gas. 0.9612 g (30 mmol) of sulfur and 15 mL of trioctylphosphine were placed in a 100 mL three-necked flask and heated to 80° C. while stirring under a nitrogen atmosphere to prepare a second compound in which sulfur was bound to trioctylphosphine. 2.3691 g (30 mmol) of selenium and 15 mL of trioctylphosphine were placed in a 100 mL three-necked flask and heated to 80° C. while stirring under a nitrogen atmosphere to prepare a third compound in which selenium was bound to trioctylphosphine. 2.5 mL of a toluene dispersion of InP core prepared in Preparation Example 1 above was prepared, 1-octadecene (15 ml) and a mixture (2.4 mL) including the first compound prepared above were put together in a three-necked flask and subjected to a process of removing the volatile components at at 110° C. under 200 mTorr for 30 minutes while stirring. Thereafter, the second compound (0.3 mL) and the third compound (0.3 mL) prepared above were placed thereto under an inert gas atmosphere and heated to 270° C. The mixture was reacted for 1 hour and cooled to synthesize an InP/ZnS$_x$Se$_{1-x}$ quantum dot as a fourth compound.

Examples 1 to 4 and Comparative Examples 1 and 3

Preparation of Quantum Dot Particle of Present Invention (1) Preparation of Quantum Dot Particle To a mixture including the fourth compound InP/ZnS$_x$Se$_{1-x}$ quantum dot prepared in Preparation Example 6 above, 30 mg of the ionic liquids of Preparation Examples 1 to 5 and two ligands of known alkyl carboxylic acids, respectively, were added, the reaction was carried out at 90° C. for 5 hours, and a ligand on the surface of the quantum dot particle was exchanged to prepare a mixture including a fifth compound, at which time the volume was confirmed. Excess ethanol was added to the mixture including the fifth compound and centrifuged to remove excess organic matter present in the quantum dot. The centrifuged supernatant was discarded, the centrifuged precipitate was dried, weighed, and dispersed in toluene to prepare quantum dot particle stable in an organic solvent.

(2) Measurement of Physical Properties of Quantum Dot Particle

The physical properties of the quantum dot particles prepared above were measured by the methods below, and the results are shown in Table 1 below.

(1) Quantum Yield (QY)

The relative quantum yield of quantum dots was calculated using a fluorescein dye (reference value for green emission dots at 440 nm excitation wavelength), based on following Equation 1, with reference to the literature of Williams et al., "Relative fluorescence quantum yields using a computer luminescence spectrometer"1983, Analyst 108: 1067.

$$QY_{dot} = QY_{st} \left( \frac{\left(\frac{I}{A}\right)_{dot}}{\left(\frac{I}{A}\right)_{st}} \right) \left( \frac{RI_{dot}^2}{RI_{st}^2} \right) \quad \text{[Equation 1]}$$

wherein, the subscript dot is a quantum dot solution dispersed in toluene, st indicates a fluorescein dye dispersed in toluene.

QY: quantum yield, I: area of emission peak, A: absorbance of excitation wavelength, RI: refractive index in solvent (2) Full Width at Half Maximum (FWHD)

The full width at half maximum was confirmed using the absorption and photoluminescence spectrum of quantum dot particles dispersed in toluene using QE-2100 (Otsuka Electronics Co.,Ltd.).

Yield (g) per 100 mL of the stock solution

For 100 mL of the quantum dot particle dispersion solution in which a ligand exchange reaction was completed, excess ethanol was added to the quantum dot particle dispersion solution in which the ligand exchange reaction was completed, and centrifuged to remove excess organic matter present in the quantum dot, discharge the centrifuged supernatant, and dry the centrifuged precipitate, and then measured mass (g) was confirmed and displayed as a proportional formula.

TABLE 1

| | Example 1 | Example 2 | Example 3 | Example 4 | Comparative Example 1 | Comparative Example 2 | Comparative Example 3 |
|---|---|---|---|---|---|---|---|
| Exchanged ligand | Preparation Example 1 | Preparation Example 2 | Preparation Example 3 | Preparation Example 4 | Preparation Example 5 | OA | DDSA |
| Yield (g) per 100 mL of the stock solution | 2.24 g | 2.19 g | 2.14 g | 2.21 g | 1.41 g | 1.16 g | 1.04 g |
| Initial quantum yield $QY_I$ (%) | 88% | 87% | 88% | 86% | 87% | 83% | 84% |
| Quantum yield after 7 days $QY_{7d}$ (%) | 78% | 77% | 79% | 78% | 43% | 30% | 32% |
| Full width at half maximum (FWHD) | 41 | 42 | 42 | 41 | 43 | 44 | 44 |

* OA: Oleic Acid  * DDSA: dodecenylsuccinic acid

As confirmed from Table 1 above, it can be seen that the quantum dot in which the ionic liquid is ion-bonded according to the present invention have remarkable effects in yield and lifespan compared with the conventional quantum dots of Comparative Examples 1 to 3.

The reason why the yield of the quantum dot in which the ionic liquid is ion-bonded according to the present invention is remarkably improved as described above seems that the ionic liquid is effectively introduced into the quantum dot particle to minimize the quantum dot particle lost during purification.

The invention claimed is:

1. A quantum dot particle comprising:
a quantum dot having a core/shell nanostructure; and
ionic liquid compounds of the following Chemical Formula 1, said ionic liquid compounds being directly bonded to surface of the quantum dot,
wherein the quantum dot and an $X^\ominus$ anion of the ionic liquid compounds form an ionic bond:

[Chemical Formula 1]

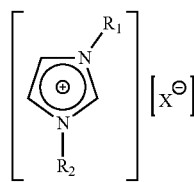

wherein,
$R_1$ and $R_2$ are each independently a branched or unbranched hydrocarbon group having 1 to 22 carbon atoms, and
$X^\ominus$ is a monovalent anion,
wherein the hydrocarbon group includes a saturated or unsaturated group.

2. The quantum dot particle according to claim 1, wherein the core of the quantum dot includes Groups III-V compounds, and the shell is doped with one or more selected from the group consisting of aluminum, silicon, titanium, magnesium, and zinc.

3. The quantum dot particle according to claim 2, wherein the core includes one or more selected from the group consisting of GaN, GaP, GaAs, GaSb, AlN, AlP, AlAs, AlSb, InN, InP, InAs, InSb, or a mixture thereof; GaNP, GaNAs, GaNSb, GaPAs, GaPSb, AlNP, AlNAs, AlNSb, AlPAs, AlPSb, InNP, InNAs, InNSb, InPAs, InPSb, or mixtures thereof; and GaAlNAs, GaAlNSb, GaAlPAs, GaAlPSb, GaInNP, GaInNAs, GaInNSb, GaInPAs, GaInPSb, GaAlNP, InAlNP, InAlNAs, InAlNSb, InAlPAs, InAlPSb, or mixtures thereof.

4. The quantum dot particle according to claim 1, wherein the core of the quantum dot includes elements In and P, and the shell includes one or more elements selected from Zn, Se, and S.

5. The quantum dot particle according to claim 1, wherein the $X^\ominus$ in the ionic liquid of Chemical Formula 1 is $Br^-$, $Cl^-$, $ClO_4^-$, $NO_3^-$, $CH_3SO_4^-$, $CH_3COO^-$, $BF_4^-$, $PF_6^-$, $CH_3COO^-$, or $(CF_3SO_2)_2N^{31}$.

6. The quantum dot particle according to claim 5, wherein the $X^\ominus$ is tetrafluoroborate ($BF_4^-$).

7. The quantum dot particle according to claim 1, wherein the ionic liquid of Chemical Formula 1 is one or more selected from the group consisting of 1-ethyl-3-methylimidazolium tetrafluoroborate, 1-propyl-3-methylimidazolium tetrafluoroborate, 1-butyl-3-methylimidazolium tetrafluoroborate, 1-heptyl-3-methylimidazolium tetrafluoroborate, 1-hexyl-3-methylimidazolium tetrafluoroborate, 1-allyl-3-methylimidazolium tetrafluoroborate, 1-(2-butenyl)-3-methylimidazolium tetrafluoroborate, 1-(2-pentenyl)-3-methylimidazolium tetrafluoroborate, 1,3-diethylimidazolium tetrafluoroborate, 1-propyl-3-ethylimidazolium tetrafluoroborate, 1-butyl-3-ethylimidazolium tetrafluoroborate, 1-hexyl-3-ethylimidazolium tetrafluoroborate, 1-allyl-3-ethylimidazolium tetrafluoroborate, 1-(2-butenyl)-3-ethylimidazolium tetrafluoroborate, and 1-(2-pentenyl)-3-ethylimidazolium tetrafluoroborate.

8. The quantum dot particle according to claim 1, wherein the ionic liquid compounds of Chemical Formula 1 are selected from the group consisting of compounds of the following Chemical Formulas 2 to 5:

[Chemical Formula 2]

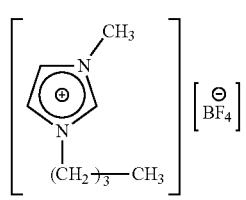

[Chemical Formula 3]

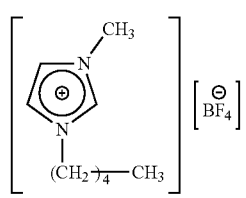

-continued

[Chemical Formula 4]

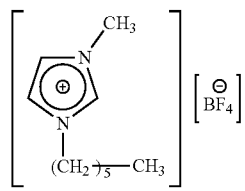

[Chemical Formula 5]

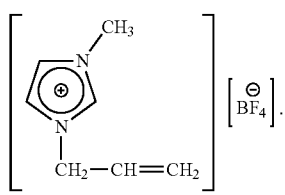

9. The quantum dot particle according to claim 1, wherein the ionic liquid compounds of Chemical Formula 1 are prepared by obtaining a compound in a salt form by reaction of an imidazole compound and an alkyl halide compound, and exchanging it with an $X^{\ominus}$ anion.

10. The quantum dot particle according to claim 1, wherein the quantum dot particle further includes a ligand coordinated to the surface of the particle.

11. The quantum dot particle according to claim 1, wherein the initial quantum yield QY is 85% or more, and the quantum yield QY after being left at room temperature of 25° C. for 7 days is 70% or more.

12. The quantum dot particle according to claim 1, wherein the particle yield after an introduction of the ionic liquid compounds into the quantum dot is 1.80 g or more per 100 mL of a quantum dot stock solution before the introduction of the ionic liquid.

13. A method of preparing a quantum dot particle, said method comprising the steps of:
(a) reacting a quantum dot having a core/shell nanostructure and ionic liquid compounds of the following Chemical Formula 1 to form an ionic bond; and
(b) recovering the quantum dot in which the ionic bond is formed in step (a),
wherein the ionic bond is formed by the bond of the quantum dot and an $X^{\ominus}$ anion of the ionic liquid compounds:

[Chemical Formula 1]

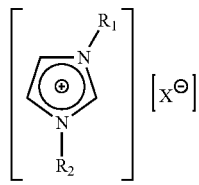

wherein,
$R_1$ and $R_2$ are each independently a branched or unbranched hydrocarbon group having 1 to 22 carbon atoms, and
$X^{\ominus}$ is a monovalent anion,
wherein the hydrocarbon group includes a saturated or unsaturated group.

* * * * *